US012667581B2

(12) United States Patent
Gomer et al.

(10) Patent No.: US 12,667,581 B2
(45) Date of Patent: Jun. 30, 2026

(54) THERAPEUTICS FOR TREATMENT OF COVID-19 SYMPTOMS

(71) Applicant: The Texas A&M University System, College Station, TX (US)

(72) Inventors: Richard H. Gomer, College Station, TX (US); Darrell Pilling, Bryan, TX (US); Tejas Karhadkar, San Mateo, CA (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 740 days.

(21) Appl. No.: 18/009,203

(22) PCT Filed: Jun. 7, 2021

(86) PCT No.: PCT/US2021/036152
§ 371 (c)(1),
(2) Date: Dec. 8, 2022

(87) PCT Pub. No.: WO2021/252347
PCT Pub. Date: Dec. 16, 2021

(65) Prior Publication Data

US 2023/0226088 A1 Jul. 20, 2023

Related U.S. Application Data

(60) Provisional application No. 63/036,915, filed on Jun. 9, 2020.

(51) Int. Cl.

| | |
|---|---|
| ***A61K 31/7012*** | (2006.01) |
| ***A61K 31/4468*** | (2006.01) |
| ***A61P 11/00*** | (2006.01) |
| ***A61P 29/00*** | (2006.01) |
| ***A61P 31/14*** | (2006.01) |

(52) U.S. Cl.
CPC ...... *A61K 31/7012* (2013.01); *A61K 31/4468* (2013.01); *A61P 11/00* (2018.01); *A61P 29/00* (2018.01); *A61P 31/14* (2018.01)

(58) Field of Classification Search
CPC . A61K 31/4468; A61K 31/7012; A61P 11/00; A61P 29/00; A61P 31/14
See application file for complete search history.

(56) References Cited

U.S. PATENT DOCUMENTS

| | | | |
|---|---|---|---|
| 5,453,533 A | 9/1995 | Luo et al. | |
| 2007/0191478 A1 | 8/2007 | Stamler et al. | |
| 2022/0133671 A1* | 5/2022 | Gomer | A61K 31/60 514/217.11 |

FOREIGN PATENT DOCUMENTS

| | | |
|---|---|---|
| CN | 111110824 A | 5/2020 |
| WO | 2005056047 | 6/2005 |
| WO | 2018049003 | 3/2018 |
| WO | 2021184123 | 9/2021 |
| WO | 2021198774 | 10/2021 |

OTHER PUBLICATIONS

Karhadkar (Scientific Reports; 2017, 7:15069, DOI:10.1038/s41598-017-15198-8). (Year: 2017).*

Extended European Search Report dated Jul. 29, 2024 from the European Patent Office for EP Application No. 21821736.2, 20 pages.

Cao Yang et al., "Ruxolitinib in treatment of severe coronavirus disease 2019 (COVID-19): A multicenter, single-blind, randomized controlled trial", Journal of Allergy and Clinical Immunology, Elsevier, Amsterdam, NL, vol. 146, No. 1, May 26, 2020, 13 pages.

Liu Jing et al., "Successful use of methylprednisolone for treating severe COVID-19", Journal of Allergy and Clinical Immunology, Elsevier, Amsterdam, NL, vol. 146, No. 2, May 29, 2020, pp. 325-327.

Wu Dandan et al., "TH17 responses in cytokine storm of COVID-19: An emerging target of JAK2 inhibitor Fedratinib", Journal of Microbiology, Immunology and Infection, Elsevier, Amsterdam, NL, vol. 53, No. 3, Mar. 11, 2020, pp. 368-370.

Jose Luis Callejas Rubio, "Eficacia de los pulsos de corticoides en pacientes con sindrome de liberacion de citocinas inducido por infeccion por SARS-CoV-2", Medicina Clinica, vol. 155, No. 4, May 27, 2020, pp. 159-161.

Pollard Bette S., et al., "Classical drug digitoxin inhibits influenza cytokine storm, with implications for COVID-19 therapy", bioRxiv, May 15, 2020, pp. 1-10.

Karhadkar Tejas R. et al., "Attenuated pulmonary fibrosis in sialidase-3 knockout ( Neu3 -/-) mice", American Journal of Physiology—Lung Cellular and Molecular Physiology, vol. 318, No. 1, Oct. 16, 2019, pp. 165-179.

Karhadkar Tejas R. et al., "Sialidase inhibitors attenuate pulmonary fibrosis in a mouse model", Scientific Reports, vol. 7, No. 1, Nov. 8, 2017, 12 pages.

Renyi Wu et al., "An Update on Current Therapeutic Drugs Treating COVID-19", Current Pharmacology Reports, vol. 6, No. 3, May 11, 2020, pp. 56-70.

George Peter M et al., "Pulmonary fibrosis and COVID-19: the potential role for antifibrotic therapy", Lancet Respir Med, vol. 8, May 15, 2020 (May 15, 2020), pp. 807-815.

Karhadkar Tejas R. et al., "Inhibiting Sialidase-Induced TGF-β1 Activation Attenuates Pulmonary Fibrosis in Mice", The Journal of Pharmacology and Experimental Therapeutics, vol. 376, Issue 1, pp. 106-117.

International Search Report and Written Opinion of International PCT Application No. PCT/US2021/036152, date of mailing Oct. 27, 2021, 11 pages.

(Continued)

*Primary Examiner* — Pancham Bakshi
(74) *Attorney, Agent, or Firm* — Jackson Walker LLP; Leisa Talbert Peschel

(57) ABSTRACT

The present disclosure relates to methods of treating Coronavirus-Associated Lung Damage (CALD) and cytokine storm using CALD-treating compounds. The methods can involve administering CALD-treating compounds to a patient suffering from CALD or cytokine storm.

37 Claims, 6 Drawing Sheets

(56) References Cited

OTHER PUBLICATIONS

Tang et al. Anticoagulant treatment is associated with decreased mortality in severe coronavirus disease 2019 patients with coagulopathy, Journal of Thrombosis and Haemostasis, vol. 18, Iss. 5, Mar. 27, 2020 [retrieved on Aug. 1, 2021]. Retrieved from the Internet: <URL: https://onlinelibrary.wiley.com/doi/full/10.1111/jth.14817>, 14 pages.

Talmor et al. Mechanical Ventilation Guided by Esophageal Pressure in Acute Lung Injury, The New England Journal of Medicine, vol. 359, No. 20, Nov. 13, 2008 [retrieved on Sep. 29, 2021]. Retrieved from the Internet: <URL: https://www.nejm.org/doi/full/10.1056/nejmoa0708638>. pp. 2095-2104.

Pubchem, SID 387058083, Available Date: Nov. 11, 2019 [retrieved on Aug. 1, 2021]. Retrieved from the Internet: <URL: https://pubchem.ncbi.nlm.nih.gov/substance/387058083>, 7 pages.

Gattinoni, L., D. Chiumello, and S. Rossi, COVID-19 pneumonia: ARDS or not? Critical Care, 2020. 24(1):p. 154).

G. Chen et al., Clinical and immunological features of severe and moderate coronavirus disease 2019, J Clin Invest.2020;130(5):2620-2629. https://doi.org/10.1172/JCI137244.

G. Kleiner et al., Cytokine levels in the serum of healthy subjects. Mediators Inflamm. 2013;2013:434010, 6 pages.

J. Gerenova et al., Serum levels of interleukin-23 and interleukin-17 in Hashimoto's thyroiditis. Acta Endocrinol (Buchar). 2019; 5(1): p. 74-79.

M.A. Forrester et al., Human interleukin-27: wide individual variation in plasma levels and complex inter-relationships with interleukin-17A. Clin Exp Immunol. 2014;178(2): p. 373-383.

S. Tian et al, Pathological study of the 2019 novel coronavirus disease (COVID-19) through postmortem core biopsies. Modern Pathology, 2020, 33:1007-1014.

H. Zhang et al., Histopathologic Changes and SARS-CoV-2 Immunostaining in the Lung of a Patient With COVID-19. Annals of Internal Medicine, 2020. 172(9): 4 pages.

S. Tian et al., Pulmonary Pathology of Early-Phase 2019 Novel Coronavirus (COVID-19) Pneumonia in Two Patients with Lung Cancer. J Thorac Oncol, 2020. 15(5): p. 700-704.

Z. Xu et al., Pathological findings of COVID-19 associated with acute respiratory distress syndrome. The Lancet Respiratory Medicine, 2020. 8(4): 4 pages.

L. Barton et al., COVID-19 Autopsies, Oklahoma, USA. Am J Clin Pathol, 2020. 153(6): 9 pages.

S. Fox et al., Pulmonary and Cardiac Pathology in Covid-19: The First Autopsy Series from New Orleans. medRxiv, 2020: p. 2020.04.06.20050575, 8 pages.

S. Felsenstein et al., COVID-19: Immunology and treatment options. Clin Immunol, 2020. 215: p. 108448. 14 pages.

M. Merad et al., Pathological inflammation in patients with COVID-19: a key role for monocytes and macrophages. Nat Rev Immunol (2020), p. 355-362. https://doi.org/10.1038/s41577-020-0331-4.

J. Rebetz et al., The Pathogenic Involvement of Neutrophils in Acute Respiratory Distress Syndrome and Transfusion-Related Acute Lung Injury, Transfusion Medicine and Hemotherapy, 2018. 45(5): p. 290-298.

D. Mcgonagle et al., The Role of Cytokines including Interleukin-6 in COVID-19 induced Pneumonia and Macrophage Activation Syndrome-Like Disease. Autoimmunity Reviews, 2020. 19(6): p. 102537, 8 pages.

P. Conti et al., Induction of pro-inflammatory cytokines (IL-1 and IL-6) and lung inflammation by Coronavirus-19 (COVID-19 or SARS-CoV-2): anti-inflammatory strategies. J Biol Regul Homeost Agents, 2020. 34(2), pp. 327-331.

N. Tang et al., Anticoagulant treatment is associated with decreased mortality in severe coronavirus disease 2019 patients with coagulopathy, Journal of Thrombosis and Haemostasis vol. 18, Issue 5 (2020) pp. 1094-1099.

N. Zareifopoulos, et al., Management of COVID-19: the risks associated with treatment are clear, but the benefits remain uncertain. Monaldi Arch Chest Dis, 2020. 90(2), 4 pages.

Reagan-Shaw et al., Dose translation from animial to human studies revisited, Faseb J., 22; 659-661 (2007).

Y. Li et al., Extraordinary GU-rich single-strand RNA identified from SARS coronavirus contributes an excessive innate immune response, Microbes and Infection 15 (2), Elsevier, 88-95 (2013).

F. Daubeuf et al., Performing Bronchoalveolar Lavage in the Mouse, Current protocols in mouse biology 2, 167-175 (2012).

N. Cox et al., DC-SIGN activation mediates the differential effects of SAP and CRP on the innate immune system and inhibits fibrosis in mice, Proceedings of the National Academy of Sciences of the United States of America, vol. 112, No. 27, 8385-8390 (2015).

D. Pilling et al., Persistent Lung Inflammation and Fibrosis in Serum Amyloid P Component (Apcs-/-) Knockout Mice, Public Library of Science One vol. 9, Issue 4, e93730 (2014), 15 pages.

T. Karhadkar et al., Sialidase inhibitors attenuate pulmonary fibrosis in a mouse model, Nature Scientific Reports 8;7 (1):15069 (2017), 12 pages.

T. Karhadkar et al., Attenuated Pulmonary Fibrosis in Sialidase-3 Knockout (Neu3-/-) Mice, American Journal of Physiology Lung Cellular and Molecular Physiology, 1;318 (1):L165-L179 (2020).

* cited by examiner

THERAPEUTICS FOR TREATMENT OF COVID-19 SYMPTOMS

CROSS-REFERENCE TO RELATED APPLICATIONS

The present application is a U.S. National Stage Application of International Application No. PCT/US2021/036152 filed Jun. 7, 2021, which claims priority to U.S. Provisional Application Ser. No. 63/036,915 filed Jun. 9, 2020, the contents of which are incorporated herein by reference in their entirety for all purposes.

STATEMENT OF GOVERNMENT INTEREST

This invention was made with government support under 1R01HL132919 awarded by the National Institutes of Health. The government has certain rights in the invention.

FIELD OF THE DISCLOSURE

The present disclosure relates to therapeutic compositions able to treat one or more COVID-19 symptoms, such as increased serum levels of interleukin-1β, increased serum levels of interleukin-6, increased serum levels of interleukin-12p70, alveolar wall thickening, increased numbers of macrophages in the lung airspaces, increased numbers of lymphocytes in the lung airspaces, or increased presence of clot-like aggregates in the lung airspaces, and more specifically, treatments for COVID-19-associated lung damage, treatments for cytokine storm, and related methods of treatment.

BACKGROUND

Severe acute respiratory syndrome coronavirus 2 (SARS-CoV-2) is a single-stranded RNA (ssRNA) virus related to severe acute respiratory syndrome coronavirus (SARS-CoV) and Middle East respiratory syndrome-related coronavirus (MERS-CoV). A SARS-CoV-2 infection can result in COVID-19, a disease characterized by unusual lung damage and reduced lung function.

SUMMARY

The present disclosure provides a method of treating COVID-19-associated lung damage (CALD) by administering a pharmaceutical formulation including a compound of formula (I):

I

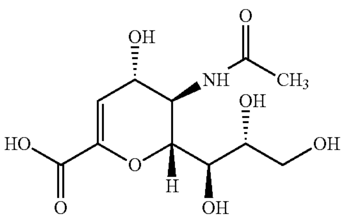

Compound I is otherwise known as 2-deoxy-2,3-didehydro-N-acetylneuraminic acid (DANA).

The present disclosure provides a method of treating CALD by administering a pharmaceutical formulation including a compound of formula (II):

II

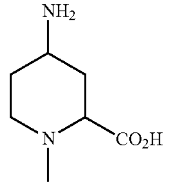

Compound II is otherwise known as 4-amino-1-methyl-2-piperidine carboxylic acid (AMPCA).

The present disclosure also provides a method for treating a cytokine storm by administering a pharmaceutical formulation including AMPCA.

The above methods may be combined with one another and alone or in combination may further include one or more of the following additional features, unless clearly mutually exclusive:

i. the method may decrease the number of cells in the lung airspace;
ii. the method may decrease the number of monocyte/macrophages in the lung airspace;
iii. the method may decrease the number of lymphocytes in the lung airspace;
iv. the method may decrease the number of clot-like aggregates in the lung airspace;
v. the method may decrease the percentage of alveoli containing non-gas material in the airspace;
vi. the method may decrease the amount of exudate in the alveoli;
vii. the method may decrease the alveolar wall thickness in the lungs;
viii. the method may decrease the levels of interleukin-1β in the blood;
ix. the method may decrease the levels of interleukin-6 in the blood;
x. the method may decrease the levels of interleukin-12p70 in the blood;
xi. the method may decrease the levels of interleukin-23 in the blood;
xii. the method may decrease the levels of interleukin-27 in the blood;
xiii. the method may decrease the patient's serum concentration of D-dimer from greater than 1 μg/ml to less than 1 μg/ml;
xiv. the patient may have a serum concentration of D-dimer greater than 1 μg/ml;
xv. the patient may have a serum concentration of interleukin-1β greater than 3 pg/ml;
xvi. the patient may have a serum concentration of interleukin-6 greater than 7 pg/ml;
xvii. the patient may have a serum concentration of interleukin-12p70 greater than 40 pg/ml;
xviii. the patient may have a serum concentration of interleukin-23 greater than 15 pg/ml; and
xix. the patient may have a serum concentration of interleukin-27 greater than 1 ng/ml.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The figures form part of the present specification and are included to further demonstrate certain aspects of the present invention. The figures are not intended to and should not be interpreted to encompass the entirety of the invention. In addition, different aspects of the invention are often illustrated as separate figures for clarity; these aspects may be combined with one another unless clearly not compatible.

FIG. 2A quantifies the number of detected monocytes/macrophages. FIG. 2B quantifies the number of detected lymphocytes. FIG. 2C quantifies the number of detected neutrophils. Points indicate individual mouse values for control (no ORN06), ORN06 and then buffer, ORN06 and then DANA, and ORN06 and then AMPCA-treated mice, respectively. Values are mean±SEM, n=6 mice (3 males and 3 females per group) for control and ORN06 with buffer; n=3 male mice for ORN06 with DANA, and n=2 male mice for ORN06 with AMPCA. For panel A, *p<0.001, **=p<0.0001 (1-way ANOVA, Bonferroni's test). For panel B, *p<0.05, (Welch's t-test).

FIG. 5A shows a lung cryosection from a mouse given PBS (control). FIG. 5B shows a lung cryosection from a mouse treated with buffer after ORN06 insult. FIG. 5C shows a lung cryosection from a mouse treated with DANA after ORN06 insult. FIG. 5D shows a lung cryosection from a mouse treated with AMPCA after ORN06 insult. The black lines on the images are the representation of the measured alveolar wall thickness. Arrow indicates an exudate in the alveolar air space. Bar is 100 μm.

FIG. 9A shows levels of IL-1β. FIG. 9B shows levels of IL-6. FIG. 9C shows levels of IL-12p70. FIG. 9D shows levels of IL-23. FIG. 9E shows levels of IL-27. Values are mean±SEM, n=6 mice (3 males and 3 females) for control and ORN06 and then buffer, n=3 male mice for ORN06 and then DANA, and n=3 male mice for ORN06 and then AMPCA. *p<0.05, **=p<0.01 (Welch's t-test).

DETAILED DESCRIPTION

Figure 1:
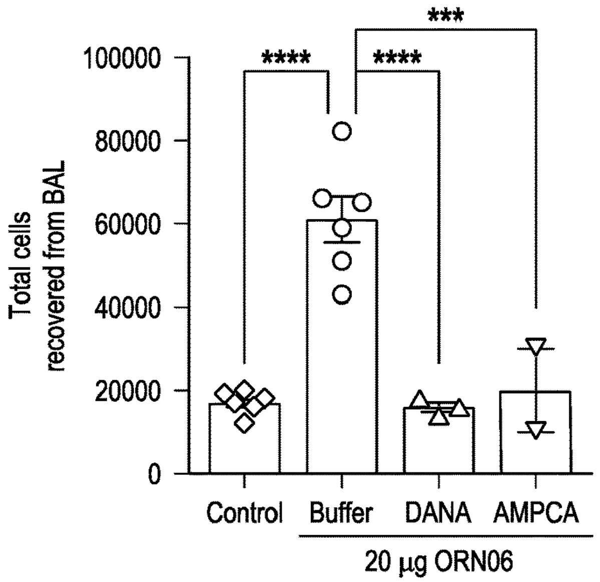
FIG. 1 is a graph quantifying the number of cells detected in mouse bronchoalveolar lavage fluid. Points indicate individual mouse values for control (no ORN06), ORN06 and then buffer, ORN06 and then DANA, and ORN06 and then AMPCA-treated mice, respectively. Values are mean±SEM, n=6 mice (3 males and 3 females per group) for control and ORN06 with buffer; n=3 male mice for ORN06 with DANA, and n=2 male mice for ORN06 with AMPCA. *p<0.001, **p<0.0001 (1-way ANOVA, Bonferroni's test).

The present disclosure relates to therapeutic compositions for treating one or more symptoms of COVID-19, which is a collection of physiological responses to infection with SARS-CoV-2 and method of treating such symptoms. In particular, the therapeutic compositions may be particularly useful in treating COVID-19-Associated Lung Damage (CALD) and cytokine storm, and methods may be particularly directed to treatment of CALD and cytokine storm. The therapeutic compositions and related methods may particularly treat or prevent abnormal blood clotting in the lungs or elsewhere and abnormally high numbers of cells in lung airspace.

As used herein, the term "COVID-19" refers to the disease caused by severe acute respiratory syndrome coronavirus 2 (SARS-CoV-2).

As used herein, the term "CALD" refers to COVID-19-associated lung damage. CALD occurs in patients suffering from COVID-19. Clinical symptoms of CALD may include relative accumulation of macrophages/monocytes in bronchoalveolar lavage fluid (BALF), severe hypoxemia, overabundance of serum cytokine levels, overabundance of serum D-dimer levels, cytokine storm, and decreased pulmonary compliance.

As used herein, the term "patient" refers to any animal, including any mammal, including, but not limited to, humans, and non-human animals (including, but not limited to, non-human primates, dogs, cats, rodents, horses, cows, pigs, mice, rats, hamsters, rabbits, and the like). In particular, the patient is a human.

As used herein, an "effective amount" is an amount sufficient to cause a beneficial or desired clinical result in a patient. An effective amount can be administered to a patient in one or more doses. It is typically administered to the patient intravenously. In terms of treatment, an effective amount is an amount that is sufficient to ameliorate the impact of and/or inhibit the induction and/or exacerbation of CALD or cytokine storm in a patient, or otherwise reduce the pathological consequences of the disease(s). The effective amount is generally determined by the physician on a case-by-case basis and is within the skill of one in the art. Several factors may be taken into account when determining an appropriate dosage to achieve an effective amount. These factors include age, the condition being treated, the severity of the condition, prior responses, and effective concentration of the composition (also referred to herein as a "treatment") being administered.

As used herein, "treat," "treating" and similar verbs refer to of ameliorating the impact of and/or inhibiting the induction and/or exacerbation of CALD or cytokine storm in a patient.

COVID-19 Causes CALD

CALD may include a variety of symptoms, including cytokine storm, increase in serum cytokine levels, relative accumulation of monocytes/macrophages in the BALF, severe hypoxemia, and decreased pulmonary compliance. See Gattinoni, L., D. Chiumello, and S. Rossi, *COVID-19 pneumonia: ARDS or not?* Critical Care, 2020. 24(1): p. 154).

One symptom of CALD is an overabundance of proinflammatory cytokines in the blood. For example, CALD is associated with elevated TNF-$\alpha$ (8.6 pg/ml (COVID-19) vs. 0.0-8.1 pg/ml (normal range)); Interleukin (IL)-1$\beta$ (5.0 pg/mL vs. 0.0-5.0 pg/ml); IL-2R (714 (455-1300) U/ml vs. 223-710 U/ml); and IL-6 (21.0 (7.5-43.4) pg/ml vs. 0.0-7.0 pg/mL). Chen et al., Clinical and immunological features of severe and moderate coronavirus disease 2019, J Clin Invest. 2020; 130(5):2620-2629. https://doi.org/10.1172/JCI137244. IL-12p70, which is normally present in serum at 34.8 (19.5-56.3) pg/ml (see Kleiner, G. et al., *Cytokine levels in the serum of healthy subjects*. Mediators Inflamm. 2013; 2013: 434010), may be elevated in the sera of patients with cytokine storm or CALD. IL-23, which is normally present in serum at 14±2 pg/ml (see Gerenova J, et al., Serum levels of interleukin-23 and interleukin-17 in Hashimoto's thyroiditis. Acta Endocrinol (Buchar). 2019;-5(1):74-79)), may be elevated in the sera of patients suffering from cytokine storm or CALD. IL-27, which is normally present in serum for most individuals at 100-1000 pg/ml (see Forrester M. et al., Human interleukin-27: wide individual variation in plasma levels and complex inter-relationships with interleukin-17A. *Clin Exp Immunol.* 2014; 178(2):373-383), may be elevated in the sera of patients suffering from cytokine storm or CALD.

Biopsy and autopsy findings indicate that CALD may be associated with the alveoli becoming filled with a cell-free protein-rich exudate, fibrin clots, lymphocytes, and macrophages. See Tian, S., et al., Pathological study of the 2019 novel coronavirus disease (COVID-19) through postmortem core biopsies. Modern Pathology, 2020; Zhang, H., et al., *Histopathologic Changes and SARS-CoV-2 Immunostaining in the Lung of a Patient With COVID-19*. Annals of Internal Medicine, 2020. 172(9): p. 629-632; Tian, S., et al., Pulmonary Pathology of Early-Phase 2019 Novel Coronavirus (COVID-19) *Pneumonia in Two Patients with Lung Cancer*. J Thorac Oncol, 2020. 15(5): p. 700-704; Xu, Z., et al., *Pathological findings of COVID-19 associated with acute respiratory distress syndrome*. The Lancet Respiratory Medicine, 2020. 8(4): p. 420-422; Barton, L. M., et al., *COVID-19 Autopsies, Oklahoma, USA*. Am J Clin Pathol, 2020. 153(6): p. 725-733; Fox, S. E., et al., *Pulmonary and Cardiac Pathology in Covid-19: The First Autopsy Series from New Orleans*. medRxiv, 2020: p. 2020.04.06.20050575. This filling of the alveoli with exudate, clots, lymphocytes, and macrophages replaces the air in the alveoli, and thus may inhibit lung function and cause hypoxemia.

CALD may also be associated with macrophages infiltrating into the lungs, which may be detected in the BALF. Severe CALD may also be associated with monocyte/macrophage activation, which may be a cause of, or associated with, a cytokine storm. Felsenstein, S., et al., COVID-19: Immunology and treatment options. Clin Immunol, 2020. 215: p. 108448. 12 and Merad, M., Martin, J. C. Pathological inflammation in patients with COVID-19: a key role for monocytes and macrophages. Nat Rev Immunol (2020). https://doi.org/10.1038/s41577-020-0331-4. This may contrast with most forms of lung damage, which are typically correlated with an accumulation of neutrophils. Neutrophils are associated with inflammation, and play a role in lung impairment resulting from ventilator-induced lung injury. See Rebetz, J., J. W. Semple, and R. Kapur, *The Pathogenic Involvement of Neutrophils in Acute Respiratory Distress Syndrome and Transfusion-Related Acute Lung Injury*. Transfusion Medicine and Hemotherapy, 2018. 45(5): p. 290-298.

Cytokine storm may be a symptom of CALD. A cytokine storm is an abnormal immune response characterized by an overabundance of cytokines, which results in an uncontrolled inflammatory response. Cytokine storm may be caused by an overabundance of macrophages/monocytes, which then produce the excessive cytokines that typify a cytokine storm. A patient suffering from cytokine storm may have increased serum levels of proinflammatory cytokines such as IL-1$\beta$, IL-6, and IL-12p70, and elevated levels of these cytokines may be associated with increased lung injury and predictive of disease severity and poor outcome. See McGonagle, D., et al., *The Role of Cytokines including Interleukin-6 in COVID-19 induced Pneumonia and Macrophage Activation Syndrome-Like Disease*. Autoimmunity Reviews, 2020. 19(6): p. 102537 and Conti, P., et al., *Induction of pro-inflammatory cytokines (IL-1 and IL-6) and lung inflammation by Coronavirus-19 (COVID-19 or SARS-CoV-2): anti-inflammatory strategies*. J Biol Regul Homeost Agents, 2020. 34(2). Other cytokines that may participate in a cytokine storm may include IL-23 and IL-27. The cytokine storm, in turn, may result in sepsis, leading to hypotension, hyper- or hypo-thermia, leukocytosis or leukopenia, and thrombocytopenia.

Other diseases may also be associated with cytokine storm. These diseases may include: Systemic juvenile idiopathic arthritis (sJIA), Adult onset Still disease, Systemic lupus erythematosus (SLE), Kawasaki disease, Periodic fever syndromes, Giant Cell Arteritis, adverse effects of immunotherapeutic agents such as CD19 CAR (chimeric antigen receptor (CAR), Blinatumomab (CD19 antibody for acute lymphoblastic leukemia, ALL), Muromonab-CD3 (OKT3) anti-T cell therapy, anti-thymocyte globulin (ATG), CD28 superagonist TGN1412, rituximab and obinutuzumab (CD20 ab, anti-B cell therapy), alemtuzumab (CD52 anti-chronic lymphocytic leukemia (CLL), and MS), brentuximab (CD30 conjugated to antimitotic agent monomethyl auristatin E (MMAE) to treat Hodgkin lymphoma (HL) and systemic anaplastic large cell lymphoma (ALCL), dacetuzumab (CD40 antibody treatment for non-Hodgkin's lymphoma and related hematological malignancies), nivolumab "Opdivo" (antibody to PD-1, to treat melanoma, lung cancer, renal cell carcinoma, Hodgkin lymphoma, head and neck cancer, colon cancer, and liver cancer), Oxaliplatin, and Lenalidomide, or infectious diseases caused by Cytomegalovirus (CMV), Epstein-Barr virus-associated Hemophagocytic Lymphohistiocytosis, Group A streptococcus, (Streptococcus pneumoniae), Influenza virus, Variola virus (Smallpox), Severe acute respiratory syndrome coronavirus (SARS-CoV), Middle East respiratory syndrome (MERS), and Avian H5N1 influenza virus.

Elevated D-dimer may also be a symptom of CALD. D-dimer is produced when blood clots dissolve in the blood. Elevated D-dimer is thus associated with the existence of blood clots. The abnormal immune response associated with CALD may cause blood clotting, thus elevating D-dimer levels. The normal level of D-dimer in the blood may be less than 0.5 μg/ml. The average level for a COVID-19 patient may be 1.94 μg/ml. Elevated D-dimer levels may be associated with poor COVID-19 outcomes. Surviving patients had an average D-dimer level of 1.94 (0.9-9.44) μg/ml. Nonsurviving patients had an average D-dimer level of 4.7 (1.42-21) μg/ml. Tang et al., Anticoagulant treatment is associated with decreased mortality in severe coronavirus disease 2019 patients with coagulopathy, Journal of Thrombosis and Haemostasis Volume 18, Issue 5 (2020) pp. 1094-99.

Hypoxemia may also be a symptom of CALD. Hypoxemia is a below-normal blood oxygen level. Hypoxemia may be indicated by a pulse oximeter reading under 90%. Severe hypoxemia may be one of the primary causes of death in COVID-19 patients.

Decreased pulmonary compliance may also be a symptom of CALD. Pulmonary compliance is a measure of lung elasticity. Thus, patients with decreased lung compliance must work harder to fill and empty their lungs. Normal lung compliance is >50 ml/cm $H_2O$. Decreased lung compliance can cause hypoxemia.

Surprisingly, only 20-30% of COVID-19 patients with severe hypoxemia also have decreased pulmonary compliance. This suggests that CALD may not typically cause hypoxemia via decreased pulmonary compliance. This results in unexpected responses to known treatments for lung damage, as most treatments focus on redressing decreased pulmonary compliance. For instance, many patients with COVID-19 respond poorly to invasive treatments normally beneficial to patients with other types of lung damage. Zareifopoulos, N., et al., *Management of COVID-19: the risks associated with treatment are clear, but the benefits remain uncertain*. Monaldi Arch Chest Dis, 2020. 90(2).

Methods of Treating CALD and Cytokine Storm

In certain embodiments, the instant disclosure is directed to methods of or uses of treatments disclosed herein in ameliorating the impact of and/or inhibiting the induction and/or exacerbation of CALD and cytokine storm in a patient by administering an effective amount of a CALD-treating compound. In certain embodiments, the methods of the present disclosure are directed to the administration of CALD-treating compounds either orally or intravenously. In other embodiments, the methods of the present disclosure are directed to the administration of CALD-treating compounds by nebulizer.

The treatment may be administered as a single dose or multiple doses. For example, but not by way of limitation, where multiple doses are administered, they may be administered at intervals of 6 times per 24 hours or 4 times per 24 hours or 3 times per 24 hours or 2 times per 24 hours or 1 time per 24 hours or 1 time every other day or 1 time every 3 days or 1 time every 4 days or 1 time per week, or 2 times per week, or 3 times per week, or once every 2 weeks, or once every 3 weeks, or once every 4 weeks. In certain embodiments, the initial dose may be greater than subsequent doses or all doses may be the same. In certain embodiments, the treatment may be continuous, for example by nebulizer or intravenous infusion or feeding tube.

In certain embodiments, the CALD-treating compound used in connection with the methods and uses of the instant disclosure is DANA as disclosed herein. In certain embodiments, the CALD-treating compound used in connection with the methods and uses of the instant disclosure is AMPCA as disclosed herein. In certain embodiments, a CALD-treating compound is administered to a patient suffering from CALD and/or cytokine storm either as a single dose or in multiple doses. The concentration of the CALD-treating compound administered is, in certain embodiments: 0.1 μM to 1,000 μM; 1 μM to 500 μM; 10 μM to 100 μM; or 20 μM to 60 μM. In certain embodiments, the CALD-treating compound is administered to a concentration of 0.1, 1, 3, or 10 mg/kg of body weight. In certain embodiments, a specific human equivalent dosage can be calculated from animal studies via body surface area comparisons, as outlined in Reagan-Shaw et al., FASEB J., 22; 659-661 (2007).

In certain embodiments, the CALD-treating compound is administered in conjunction with one or more additional therapeutics. The one or more additional therapeutics may include a CALD-treating compound.

In certain embodiments, the CALD-treating compound is administered to a patient diagnosed with COVID-19.

In certain embodiments, the CALD-treating compound is administered to a patient with an oxygen level less than 90% as measured by pulse oximetry.

In certain embodiments, the CALD-treating compound is administered to a patient with a pulmonary compliance of greater than 50 ml/cm $H_2O$.

In certain embodiments, the CALD-treating compound is administered to a patient having D-dimer serum concentration greater than 0.5, 1, 1.5, 2, 2.5, 5, 10, or 20 μg/ml.

In certain embodiments, the CALD-treating compound is administered to a patient having a IL-1β serum concentration greater than 3, 3.5, 4, 4.5, or 5 pg/ml.

In certain embodiments, the CALD-treating compound is administered to a patient having an IL-6 serum concentration greater than 7, 8, 9, 10, 15, 20, 25, 30, 35, or 40 pg/ml.

In certain embodiments, the CALD-treating compound is administered to a patient having a IL-12p70 serum concentration greater than 40, 45, 50, 55, or 60 pg/ml.

In certain embodiments, the CALD-treating compound is administered to a patient having a IL-23 serum concentration greater than 15, 17, 19, 25, or 30 pg/ml.

In certain embodiments, the CALD-treating compound is administered to a patient having a IL-27 serum concentration greater than 1, 2, 3, 4, 5, 10, or 20 ng/ml.

CALD-Treating Compounds

In some embodiments a compound of formula (I) serves as a CALD-treating compound.

I

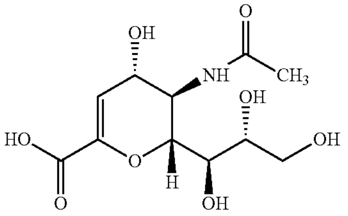

Compound I is otherwise known as 2-deoxy-2,3-didehydro-N-acetylneuraminic acid (DANA). DANA may reduce the accumulation of inflammatory cells in lung airspaces. This reduction may treat CALD.

In some embodiments a compound of formula (II) serves as a CALD-treating compound.

II

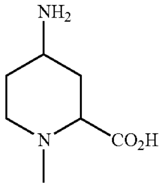

Compound II is otherwise known as 4-amino-1-methyl-2-piperidine carboxylic acid (AMPCA). AMPCA may reduce the accumulation of inflammatory cells in lung airspaces. This reduction may treat CALD and cytokine storm.

CALD-Treating Pharmaceutical Formulations

In certain embodiments, the CALD-treating compounds of the present disclosure are formulated for intravenous administration. For intravenous administration, a solution or suspension containing the CALD-treating compound can be formulated by conventional means, for example with hypodermic needle. In certain embodiments, the CALD-treating compound of the present disclosure is formulated in isotonic saline. In certain embodiments, the CALD-treating compound of the present disclosure is formulated in PBS (5.6 mM sodium phosphate, dibasic, 1.06 mM potassium phosphate, monobasic, 154 mM sodium chloride, pH 7.4).

In certain embodiments, the CALD-treating compounds of the present disclosure are formulated for inhalation administration.

In certain embodiments, the CALD-treating compounds of the present disclosure are formulated for oral administration.

To facilitate delivery to a cell, tissue, or subject, the CALD-treating compound of the present disclosure may, in various compositions, be formulated with a pharmaceutically-acceptable carrier, excipient, or diluent. The term "pharmaceutically-acceptable", as used herein, means that the carrier, excipient, or diluent of choice does not adversely affect the biological activity of the CALD-treating compound. Suitable pharmaceutical carriers, excipients, and/or diluents for use in the present disclosure include, but are not limited to, lactose, sucrose, starch powder, talc powder, cellulose esters of alkonoic acids, magnesium stearate, magnesium oxide, crystalline cellulose, methyl cellulose, sorbitol, carboxymethyl cellulose, gelatin, glycerin, sodium alginate, gum arabic, acacia gum, sodium and calcium salts of phosphoric and sulfuric acids, polyvinylpyrrolidone and/or polyvinyl alcohol, polysorbate 20, saline, and water. Specific pharmaceutical formulations of compounds for therapeutic treatment are discussed in Hoover, J. E., Remington's Pharmaceutical Sciences (Easton, Pa.: Mack Publishing Co., 1975) and Liberman and Lachman, eds. Pharmaceutical Dosage Forms (New York, N.Y.: Marcel Decker Publishers, 1980).

In accordance with the methods of the present disclosure, the quantity of the CALD-treating compound that is administered to a cell, tissue, or subject should be an effective amount.

The above methods may be combined with one another and alone or in combination may further include one or more of the following additional features, unless clearly mutually exclusive:

i. the method may decrease the number of cells in the lung airspace;
ii. the method may decrease the number of monocyte/macrophages in the lung airspace;
iii. the method may decrease the number of lymphocytes in the lung airspace;
iv. the method may decrease the number of clot-like aggregates in the lung airspace;
v. the method may decrease the percentage of alveoli containing non-gas material in the airspace;
vi. the method may decrease the amount of exudate in the alveoli;
vii. the method may decrease the alveolar wall thickness in the lungs;
viii. the method may decrease the levels of interleukin-1β in the blood;
ix. the method may decrease the levels of interleukin-6 in the blood;
x. the method may decrease the levels of interleukin-12p70 in the blood;
xi. the method may decrease the levels of interleukin-23 in the blood;
xii. the method may decrease the levels of interleukin-27 in the blood;
xiii. the method may decrease the patient's serum concentration of D-dimer from greater than 1 μg/ml to less than 1 μg/ml;
xiv. the patient may have a serum concentration of D-dimer greater than 1 μg/ml;
xv. the patient may have a serum concentration of interleukin-1β greater than 3 pg/ml;
xvi. the patient may have a serum concentration of interleukin-6 greater than 7 pg/ml;
xvii. the patient may have a serum concentration of interleukin-12p70 greater than 40 pg/ml;
xviii. the patient may have a serum concentration of interleukin-23 greater than 15 pg/ml; and
xix. the patient may have a serum concentration of interleukin-27 greater than 1 ng/ml.

EXAMPLES

The following examples illustrate aspects of the invention; no example is intended to encompass the invention as a whole. Furthermore, although some examples may present discrete embodiments of the invention, aspects of such examples may be combined with other variations of the invention as described above or in different examples unless such combinations would be clearly inoperable to one of skill in the art.

Example 1: DANA and AMPCA Reduce the Accumulation of Cells, Specifically Monocyte/Macrophages, in the Lung Airspace of a Mouse Model of CALD Administration of ssRNA oligonucleotide with 6 UUGU repeats (ORN06) is a model for CALD. Li et al., *Extraordinary GU-rich single-strand RNA identified from SARS coronavirus contributes an excessive innate immune response*, Microbes and Infection 15 (2), 88-95 (2013). Addition of the oligonucleotide leads to pulmonary edema, accumulation of inflammatory cells in the airspaces in the lungs, and alveolar hemorrhage/damage.

To determine if DANA or AMPCA affect CALD symptoms in mice, 5 week old 20 g male and female C57BL/6 mice (#000664; Jackson Laboratories, Bar Harbor, ME) were given an oropharyngeal aspiration of 1 mg/kg (20 μg/mouse) ORN06/LyoVec (LyoVec protects the ssRNA from degradation and facilitates cellular uptake) (InvivoGen, San Diego, CA) in 50 μl phosphate-buffered saline (PBS) to induce symptoms of pulmonary inflammation, or an oropharyngeal aspiration of an equal volume of PBS as a control, following *Current protocols in mouse biology* 2, 167-175 (2012). At 24 and 48 hours after ORN06 insult, some of ORN06-treated mice were given intraperitoneal injections of 100 μl PBS, or 10 mg/kg of DANA (N-Acetyl-2,3-dehydro-2-deoxyneuraminic acid; #252926-10MG, EMD, Millipore, Burlington, MA) or 0.1 mg/kg of 2-piperidinecarboxylic acid, 4-amino-1-methyl (AMPCA, #A00285-13785-026, Sundia, Shanghai, China) in 100 μl PBS. The DANA was dissolved in water to 2.5 mg/ml, and then diluted in PBS The AMPCA was dissolved directly in PBS. At day 3, mice were euthanized by $CO_2$ inhalation, and BALF was obtained as previously described in *Current protocols in mouse biology* 2, 167-175 (2012); *Proceedings of the National Academy of Sciences of the United States of America* 112, 8385-8390 (2015); *Public Library of Science ONE* 9, e93730 (2014); and *Nature Scientific Reports* 8; 7 (1):15069 (2017). The experiment was performed in accordance with the recommendations in the Guide for the Care and use of Laboratory Animals of the National Institutes of Health. The Texas A&M University Animal Use and Care Committee approved the protocol.

Total cells in the BALF were then quantified. The BALF cells were processed to prepare cell spots as described previously in *Public Library of Science ONE* 9, e93730 (2014), *Nature Scientific Reports* 8; 7 (1):15069 (2017); *American Journal of Physiology Lung Cellular and Molecular Physiology,* 1; 318 (1):L165-L179 (2020). After air drying for 48 hours at room temperature, some of the prepared BALF cell spots were fixed and treated with Wright-Giemsa stain (#08711, Polysciences, Inc., Warrington, PA) following the manufacturer's instructions. One hundred and fifty cells per mouse were examined and quantified for cell type following the manufacturer's instructions. Imaging of BALF cell spots stained with Wright-Giemsa stain was done with a Nikon Eclipse Ti2 microscope.

Results of total cell counts are presented in FIG. 1. Compared to control, a 20 μg dose of ORN06 caused a large increase in the number of cells recovered from the BALF, similar to what happens in a very ill COVID-19 patient. DANA and AMPCA treatments ameliorated the ORN06-induced increase in the number of cells in the BALF. There is no significant difference observed in the Control group and the DANA-treated or AMPCA-treated groups. Values are mean±SEM, n=6 mice (3 males and 3 females per group) for control and ORN06 with buffer; n=3 male mice for ORN06 with DANA, and n=2 male mice for ORN06 with AMPCA. *p<0.001, **p<0.0001 (1-way ANOVA, Bonferroni's test).

Figure 2A:
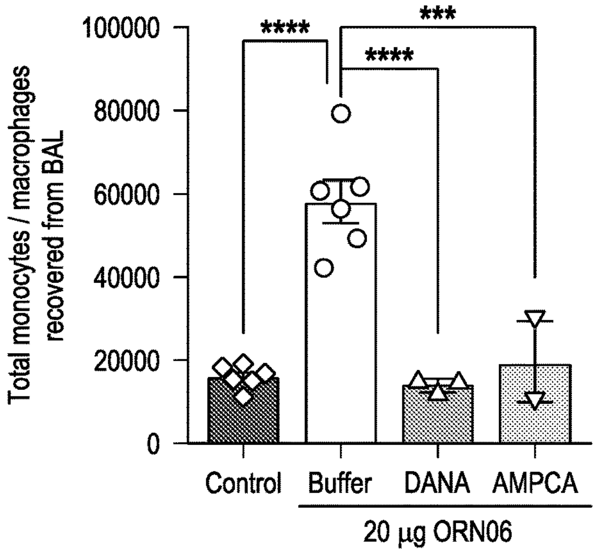
FIGS. 2A-2C are graphs quantifying the number of immune cells detected in mouse bronchoalveolar lavage fluid by Wright-Giemsa staining.
Figure 2B:
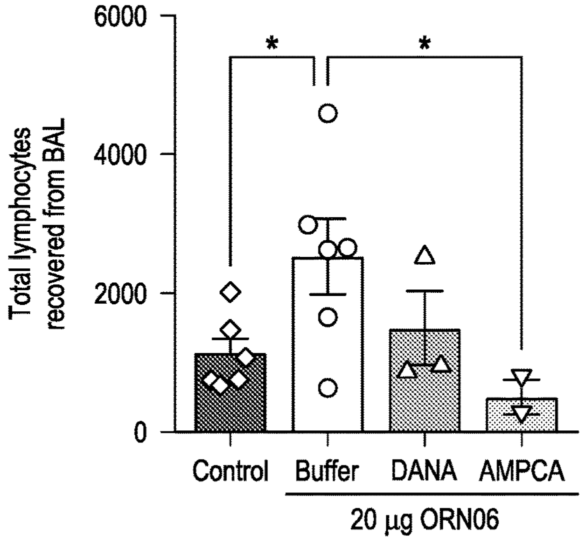
Figure 2C:
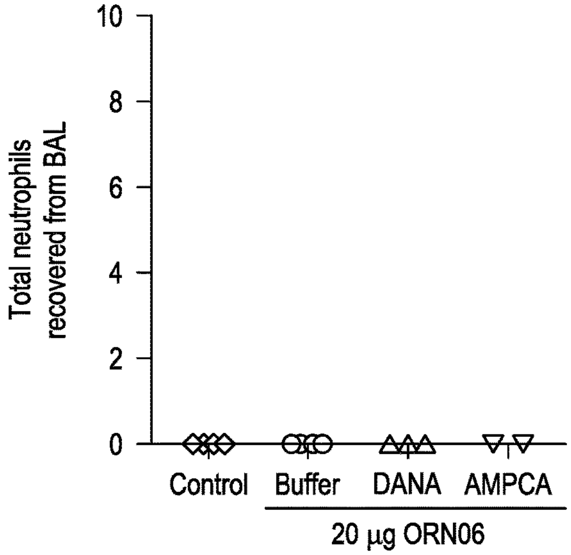

Results of counts of specific cell types from Wright-Giemsa staining are presented in FIG. 2A-C. Compared to control, a 20 μg dose of ORN06 caused a large increase in the number of monocyte/macrophages and lymphocytes. DANA treatments decreased the ORN06-induced increase in the number of monocyte/macrophages in the BALF. AMPCA treatments decreased the ORN06-induced increase in the number of monocyte/macrophages and lymphocytes in the BALF. There is no significant difference observed between the Control group and the DANA or AMPCA-treated groups. The ORN06 treatment did not significantly increase the number of neutrophils in the BALF. Values are mean±SEM, n=6 mice (3 males and 3 females per group) for control and ORN06 with buffer; n=3 male mice for ORN06 with DANA, and n=2 male mice for ORN06 with AMPCA. For panel A, *p<0.001, **=p<0.0001 (1-way ANOVA, Bonferroni's test). For panel B, *p<0.05, (Welch's t-test).

Immunochemistry on BALF cell spots and counts of cells was performed as described previously in *Public Library of Science ONE* 9, e93730 (2014); *Proceedings of the National Academy of Sciences of the United States of America* 112, 8385-8390 (2015); *Nature Scientific Reports* 8; 7 (1):15069 (2017); *American Journal of Physiology Lung Cellular and Molecular Physiology,* 1; 318 (1)1,165-L179 (2020) using anti-CD3 (100202, clone 17A2, BioLegend, San Diego, CA) to detect T-cells, anti-CD11b (101202, clone M1/70, BioLegend) to detect blood and inflammatory macrophages, anti-CD11c (M100-3, clone 223H7, MBL International, Woburn, MA) to detect alveolar macrophages and dendritic cells, anti-CD45 (103102, clone 30-F11, BioLegend) for total leukocytes, anti-Ly6G (127602, clone 1A8, BioLegend) to detect neutrophils, with isotype-matched irrelevant rat antibodies diluted to 5 μg/ml in PBS containing 2% (w:v) bovine serum albumin (PBS-BSA) (VWR, Radnor, PA). Cells were then incubated in coplin jars containing PBS, with 6 changes of buffer over 30 minutes. Cell spots were then incubated with 1 μg/ml biotin-conjugated F(ab')2-donkey anti-rat antibodies from Novus Biologicals (Littleton, CO) in PBS-BSA for 30 minutes at room temperature. Cells were then incubated in coplin jars containing PBS, with 6 changes of buffer over 30 minutes. Cell spots were then incubated with a 1/1000 dilution of streptavidin-conjugated alkaline phosphatase staining (Vector Laboratories, Burlingame, CA) in PBS-BSA. Staining was developed with the Vector Red Alkaline Phosphatase Kit (Vector Laboratories) for 4 minutes at room temperature following the manufacturer's directions. Cells were counterstained with Gill's hematoxylin #3 (Sigma-Aldrich, St. Louis, MO), air dried overnight, and then coverslip (VWR) mounted in Permount mounting medium (17986-01, Electron Microscopy Sciences, Hatfield, PA). Using a 40× objective, at least 100 cells from each stained BALF spot were examined and the percent positive cells was recorded.

Figure 3:
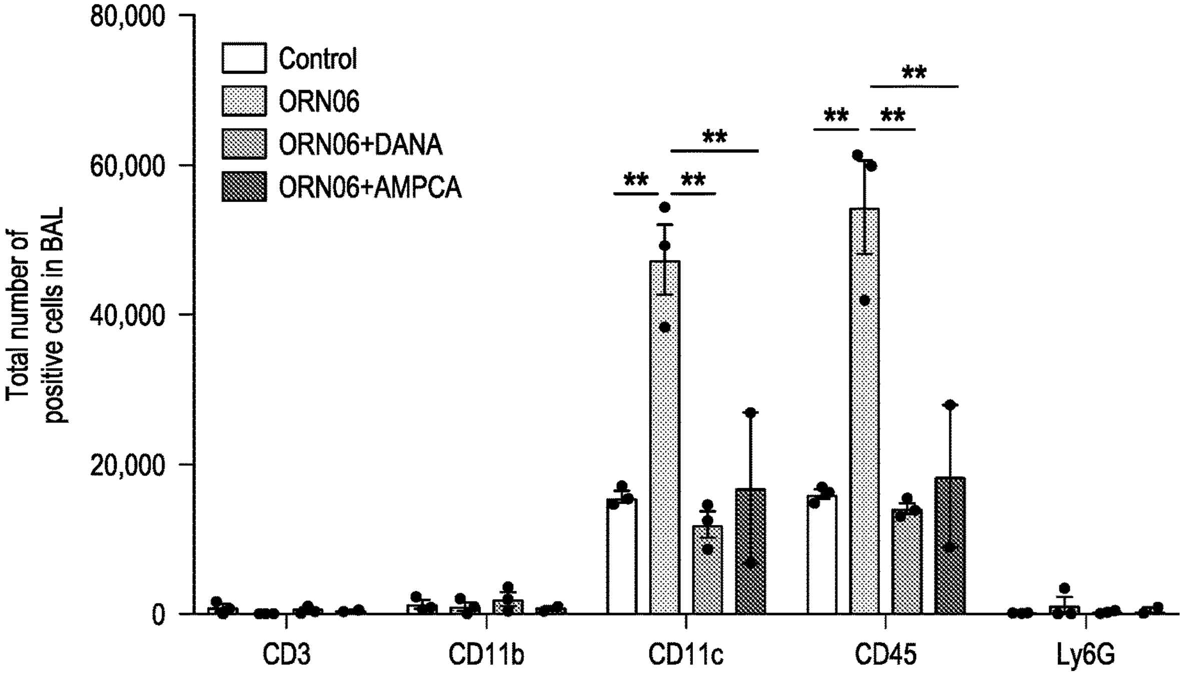
FIG. 3 is a graph quantifying the number of immune cells detected by immunocytochemistry in mouse bronchoalveolar lavage fluid. Points indicate individual mouse values for control (no ORN06), ORN06 and then buffer, ORN06 and then DANA, and ORN06 and then AMPCA-treated mice, respectively. Values are mean±SEM, n=3 male mice, and n=2 male mice for ORN06 with AMPCA. **p<0.01 (1-way ANOVA, Dunnett's test).

Results of counts of specific cell types from immunohistochemistry staining are presented in FIG. 3. Compared to control, a 20 μg dose of ORN06 caused a large increase in the number of CD11c-positive macrophages and/or dendritic cells, and a large increase in the number of CD45-positive leukocytes. DANA or AMPCA treatments decreased the ORN06-induced increase in the number of CD11c positive macrophages and/or dendritic cells, and CD45-positive leukocytes in the BALF. The ORN06 treatment did not significantly increase the number of Ly6G-positive neutrophils in the BALF. Values are mean±SEM, n=3 male mice, and n=2 male mice for ORN06 with AMPCA. **p<0.01 (1-way ANOVA, Dunnett's test). Together, these results indicate that DANA and AMPCA injections can inhibit an excessive accumulation of monocytes/macrophages and lymphocytes in the lung airspace.

Figure 4:
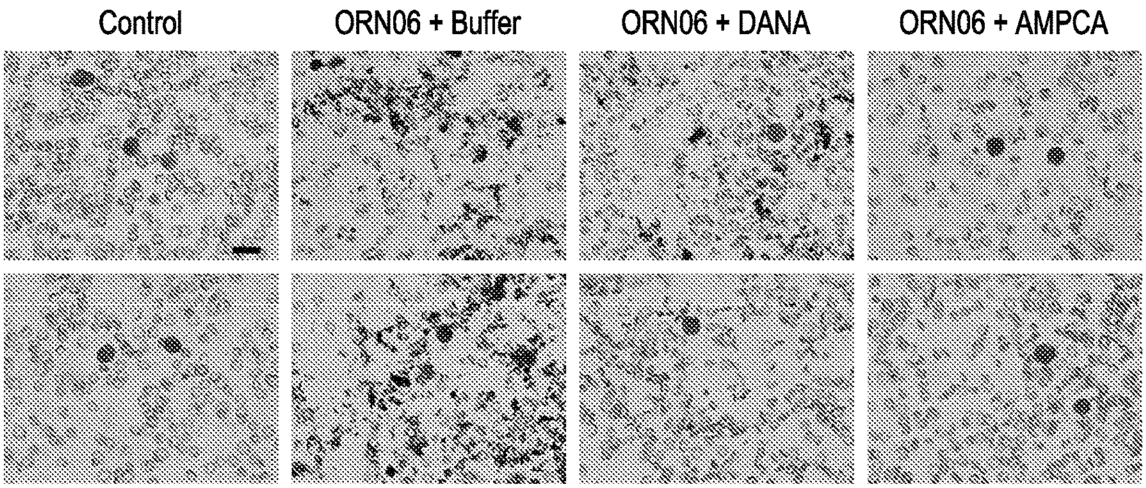
FIG. 4 is a photomicrograph of Wright-Giemsa staining of bronchoalveolar lavage fluid cell spots from mice. The left two images are of bronchoalveolar lavage fluid cell spots from two different control male mice. The next two images are of bronchoalveolar lavage fluid cell spots from two different male mice treated with buffer after ORN06 insult. The next two images are of bronchoalveolar lavage fluid cell spots from two different male mice treated with DANA after ORN06 insult. The right two images are of bronchoalveolar lavage fluid cell spots from two different male mice treated with AMPCA after ORN06 insult. Bar is 10 μm.
Figure 5A:
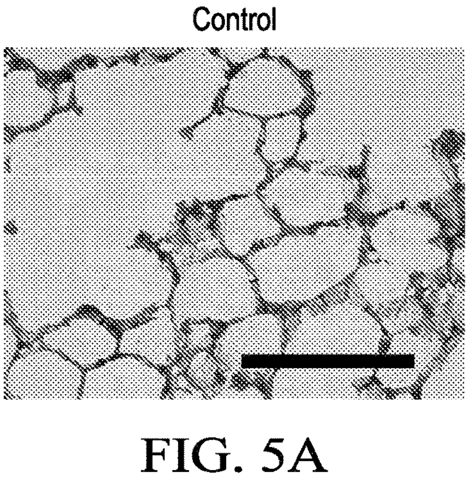
FIGS. 5A-5D are photomicrographs of hematoxylin-and-eosin-stained lung cryosections from male mice.
Figure 5B:
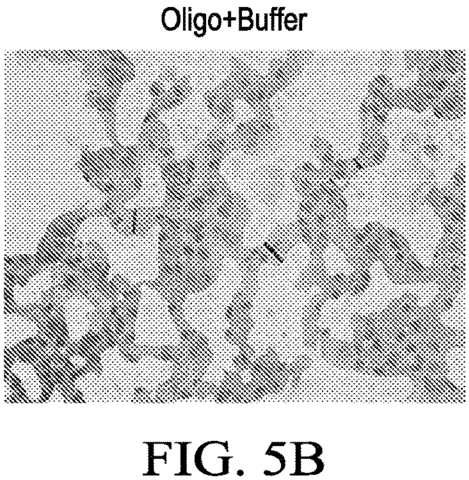
Figure 5C:
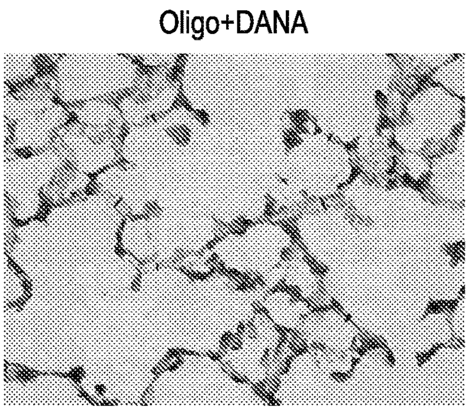
Figure 5D:
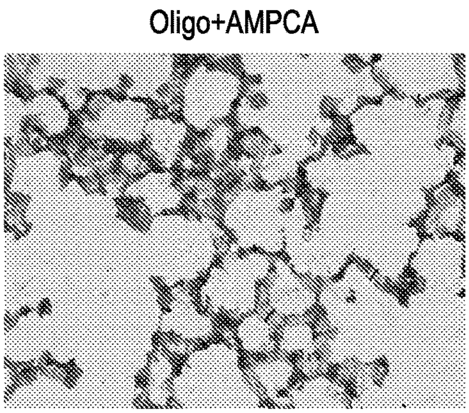

Example 2: DANA and AMPCA Reduce the Accumulation of Clot-Like Aggregates in the Lung Fluid in a Mouse Model of CALD The BALF cell spots were imaged with a 100× oil immersion objective. As shown in FIG. 4, the ORN06 treatment with subsequent buffer injections caused the formation of irregular clot-like aggregates (dark blue) in the BALF from 2 of 3 male mice, similar to the platelet-rich clots seen in COVID-19 patient lungs after autopsy. Defining a clot-like aggregate as an irregularly shaped 2-10 μm object in the BALF staining dark blue with Wright-Giemsa stain, no clot-like aggregates were observed in the BAL cell spots from 2 of the 3 male ORN06-treated with subsequent DANA injections mice (1 mouse in this group had some clot-like aggregates, but these were far fewer than in the male ORN06-treated with subsequent buffer injections mice). No clot-like aggregates were observed in the BAL cell spot from 2 male ORN06-treated with subsequent AMPCA injections mice (the BAL was lost for the third mouse in this group). These results indicate that DANA and AMPCA injections can inhibit the formation of clot-like aggregates in the lungs.

Example 3: DANA and AMPCA Reduce Alveolar Wall Thickening in the Lungs in a Mouse Model of CALD After collecting BALF, the lungs from the mice were harvested and inflated with Surgipath frozen section compound (#3801480, Leica, Buffalo Grove, IL) and preserved at −80° C. 10 μm cryosections of lungs were placed on glass slides (#48311-703, VWR) and were air dried for 48 hours. Cryosections were fixed in acetone for 20 minutes, and then air dried. The cryosections were incubated for 5 minutes in water at room temperature and then stained for two minutes at room temperature with Gill's hematoxylin No. 3 solution (#GH332-1L, Sigma-Aldrich, St. Louis, MO) diluted 1:3 with water to counterstain the cryosections and then rinsed under tap water for 1 minute at room temperature. The slides were then incubated with 0.1% eosin for 1 minute at room temperature and then washed by dipping in water for 10 seconds at room temperature. The stained slides were allowed to dry for 2 hours at room temperature; cleared with xylenes (#MK866816, VWR); and mounted with Permount mounting medium (#17986-01, VWR). After drying the mounted slides for 48 hours at room temperature, light microscopy images were captured using a 40× objective on a Nikon Eclipse Ti2 microscope (Nikon, Melville, NY). Images of a 1 mm calibration slide (#MA663, Swift Microscope World, Carlsbad, CA) were used for size bars. Three fields of view were chosen randomly and the images were captured with Amscope (Irvine, CA). Image quantification was done using Image J (NIH, Bethesda, MD). Using the Set Scale function from Image J on a 1 mm scale bar image, all the images were calibrated to the same scale by applying the settings globally. Using ' Straight' command, the length of the alveolar wall on the image was measured and was recorded with the 'Measure' command. 8 measurements of the alveolar wall thickness were recorded for each image. The measurements were processed in Prism (Graphpad, La Jolla, CA).

Figure 6:
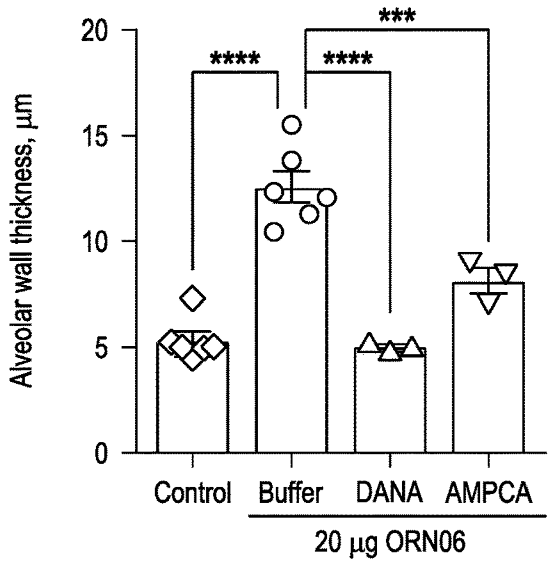
FIG. 6 is a graph quantifying alveolar wall thickness in lung cryosections. Points indicate individual mouse values for control (no ORN06), ORN06 and then buffer, ORN06 and then DANA, and ORN06 and then AMPCA-treated mice, respectively. Values are mean±SEM, n=6 mice (3 males and 3 females per group) for control and ORN06 with buffer; n=3 male mice for ORN06 with DANA, and n=3 male mice for ORN06 with AMPCA. *p<0.001, **=p<0.0001 (1-way ANOVA, Bonferroni's test).

As shown in FIGS. 5 and 6, compared to the control group, ORN06 aspirated and buffer-injected mice showed a significant increase in alveolar wall thickness. The ORN06-induced alveolar wall thickness increase was significantly reduced by treatment with DANA or AMPCA. Values are mean±SEM, n=6 mice (3 males and 3 females per group) for control and ORN06 with buffer; n=3 male mice for ORN06 with DANA, and n=3 male mice for ORN06 with AMPCA. *p<0.001, **=p<0.0001 (1-way ANOVA, Bonferroni's test). These results indicate that DANA and AMPCA injections can inhibit an excessive alveolar wall thickening in the lungs.

Figure 7:
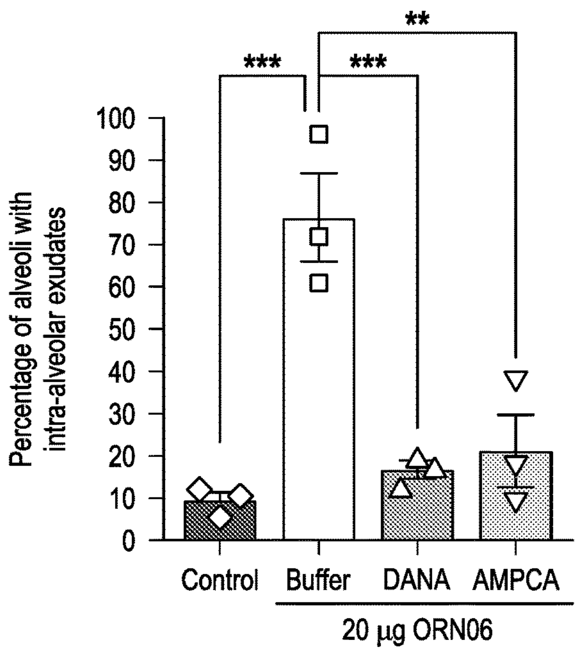
FIG. 7 is a graph quantifying the percentage of alveoli containing one or more exudates in the alveolar airspace observed in lung-section micrographs. Points indicate individual mouse values for control (no ORN06), ORN06 and then buffer, ORN06 and then DANA, and ORN06 and then AMPCA-treated mice, respectively. Values are mean±SEM, n=3 male mice. p<0.01, *=p<0.001 (1-way ANOVA, Bonferroni's test).

Example 4: DANA and AMPCA Reduce the Percentage of Exudate-Containing Alveoli and Reduce the Volume of the Alveolar Airspace Occupied by Exudate in a Mouse Model of CALD Also as shown by the arrow in FIG. 5, oropharyngeal aspiration of ORN06 in mice causes the formation of exudates visible as light pink objects in the interior of alveoli (the alveolar airspace) in cryosections stained with hematoxylin & eosin. For each mouse, for the cryosections described in Example 3, 3 randomly chosen fields of view were photographed with a 20× objective on a Nikon Eclipse Ti2 microscope, and both the number of exudate-containing alveoli and exudate-free alveoli in each image were counted. The percent of exudate-containing alveoli was then calculated. As shown in FIG. 7, ORN06 treatment caused the percentage of exudate-containing alveoli to increase. DANA or AMPCA treatments after ORN06 treatment decreased the percentage of exudate-containing alveoli. Values are mean±SEM, n=3 male mice. p<0.01, *=p<0.001 (1-way ANOVA, Bonferroni's test).

Figure 8:
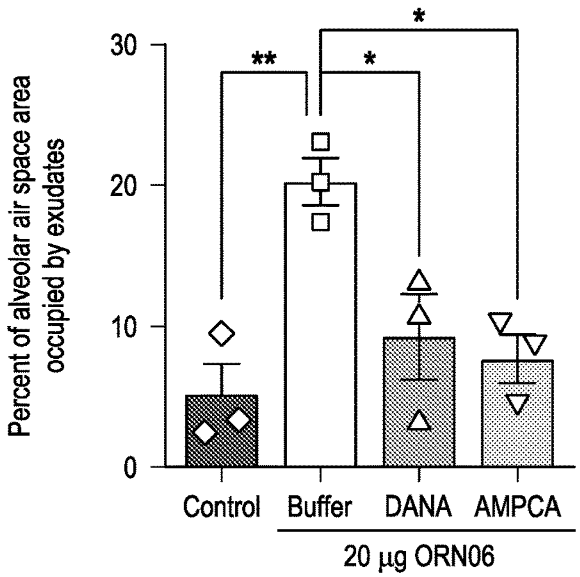
FIG. 8 is a graph quantifying the percentage area of alveoli airspace containing exudate observed in micrographs of lung sections. Points indicate individual mouse values for control (no ORN06), ORN06 and then buffer, ORN06 and then DANA, and ORN06 and then AMPCA-treated mice, respectively. Values are mean±SEM, n=3 male mice. *p<0.05, **=p<0.01 (1-way ANOVA, Bonferroni's test).
Figure 9A:
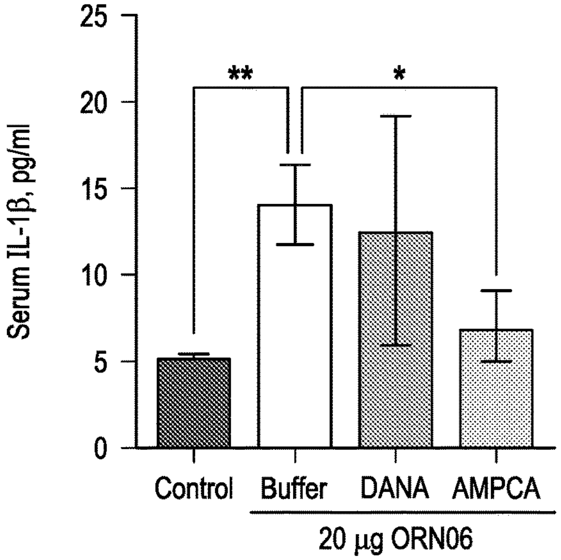
FIGS. 9A-9E are graphs quantifying cytokine levels detected in mouse serum for control (no ORN06), ORN06 and then buffer, ORN06 and then DANA, and ORN06 and then AMPCA-treated mice, respectively. BLD indicates below level of detection.
Figure 9B:
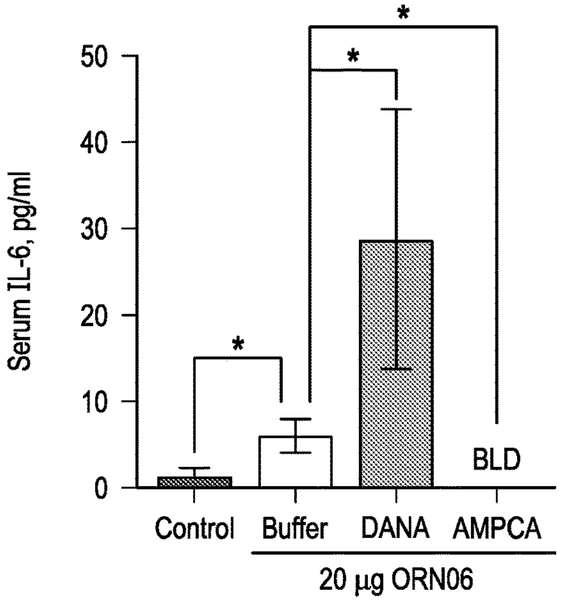
Figure 9C:
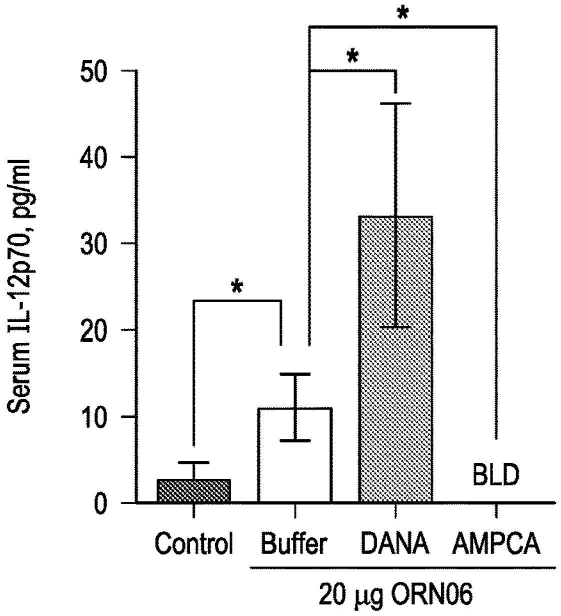
Figure 9D:
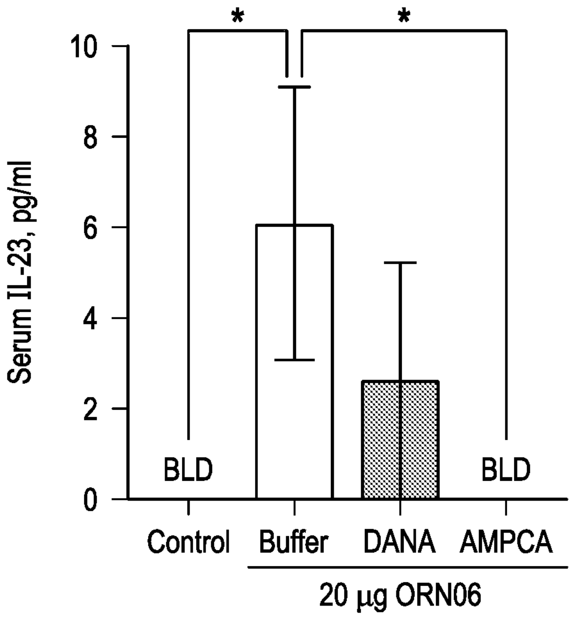
Figure 9E:
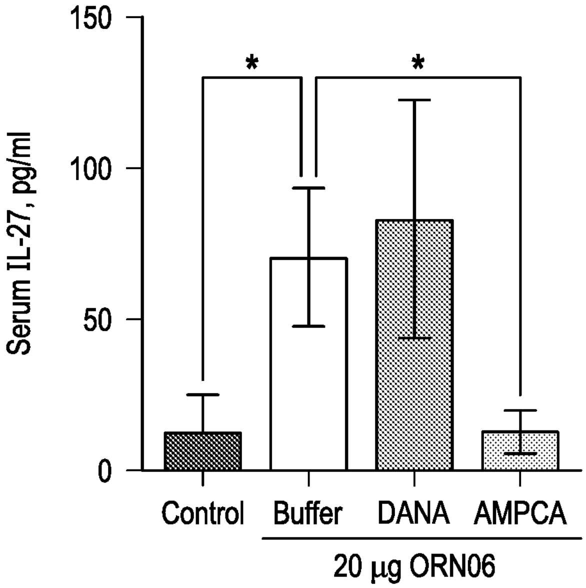

Using the Threshold function and the Measure Tool in NIH ImageJ, the percent area of each 20× objective image of lung cryosections described above containing tissue (not counting pale pink exudates) was measured, and this percentage was subtracted from 100% to obtain the percent area of the image occupied by the alveolar airspace. The threshold was then adjusted to obtain the percent area of the image occupied by tissue and exudate. The percent area of the image occupied by exudate was then calculated by subtracting the percent area of the image occupied by tissue from the percent area of the image occupied by tissue and exudate. The percentage of the exudate-occupied airspace area was then calculated by taking the ratio of (percent area of the image occupied by exudate)/(percent area of the image occupied by the alveolar airspace), and converting the fraction to a percentage. As shown in FIG. 8, ORN06 treatment caused the percentage of the alveolar airspace area occupied by exudate to increase. DANA or AMPCA treatments after ORN06 treatment decreased the percentage of the alveolar airspace area occupied by exudate. Values are mean±SEM, n=3 male mice. Values are mean±SEM, n=6 mice (3 males and 3 females) for control and ORN06 and then buffer, n=3 male mice for ORN06 and then DANA, and n=3 male mice for ORN06 and then AMPCA. *p<0.05, **=p<0.01 (1-way ANOVA, Bonferroni's test). Together, these results indicate that DANA and AMPCA injections can inhibit an excessive accumulation of exudate material in the alveolar airspace in the lungs.

Example 5: AMPCA Reduces Serum Cytokine Levels in a Mouse Model of COVID-19-Like Cytokine Storm Serum samples collected at day 3 post control or ORN06 insult were processed following the manufacturer's protocol. (#740150, LEGENDplex Mouse Inflammation Panel (13-plex), Biolegend, San Diego, CA) for simultaneous quantification of mouse cytokines using an Accuri C6 (BD Bioscience, Franklin Lakes, NJ) flow cytometer.

As shown in FIG. 9, compared to control, the ORN06 treatment of mice caused serum concentrations of IL-1β (FIG. 9A) and IL-6 (FIG. 9B) to increase. For the ORN06-treated mice, AMPCA injections decreased the serum levels of both cytokines. Other cytokines that may participate in a cytokine storm include IL-12p70, IL-23 and IL-27. Compared to control, ORN06 treatment of mice caused serum concentrations of IL-12p70 (FIG. 9C), IL-23 (FIG. 9D), and IL-27 (FIG. 9E) to increase. AMPCA injections decreased the serum levels of IL-12p70, IL-23, and IL-27 in ORN06-treated mice. $*=p<0.05$, $**=p<0.01$ (Welch's t test). Together, these results strongly suggest that AMPCA could be a useful therapeutic to treat patients with CALD or a cytokine storm.

The above disclosed subject matter is to be considered illustrative, and not restrictive, and the appended claims are intended to cover all such modifications, enhancements, and other embodiments which fall within the true spirit and scope of the present disclosure. For example, although the disclosure focuses on treatment of CALD, CALD-treating compounds might also be effective in treating diseases causing overactivation of the immune system, such as other cytokine-storm-causing diseases.

The invention claimed is:

1. A method of treating COVID-19-associated lung damage (CALD), the method comprising administering to a patient with COVID-19 an effective amount of a pharmaceutical formulation comprising compound II

II

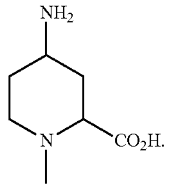

2. The method of claim 1, wherein the patient has a serum concentration of D-dimer greater than 1 μg/ml.

3. The method of claim 1, wherein the patient has a serum concentration of interleukin-1β greater than 3 pg/ml.

4. The method of claim 1, wherein the patient has a serum concentration of interleukin-6 greater than 7 pg/ml.

5. The method of claim 1, wherein the administration results in a decrease of an amount of D-dimer in the patient's blood from greater than 1 μg/ml to less than 1 μg/ml.

6. A method of treating CALD, the method comprising administering to a patient having an oxygen level of less than 90% as measured by pulse oximetry and a pulmonary compliance of greater than 50 ml/cm $H_2O$ an effective amount of a pharmaceutical formulation comprising compound II.

7. The method of claim 6, wherein the patient has a serum concentration of D-dimer greater than 1 μg/ml.

8. The method of claim 6, wherein the patient has a serum concentration of interleukin-1β greater than 3 pg/ml.

9. The method of claim 6, wherein the patient has a serum concentration of interleukin-6 greater than 7 pg/ml.

10. The method of claim 6, wherein the administration results in a decrease of an amount of D-dimer in the patient's blood from greater than 1 μg/ml to less than 1 μg/ml.

11. A method of treatment of cytokine storm, the method comprising administering to a patient having a serum level of interleukin-1β greater than 3.2 pg/ml an effective amount of a pharmaceutical formulation comprising compound II.

12. The method of claim 11, wherein the patient has a serum concentration of D-dimer greater than 1 μg/ml.

13. The method of claim 11, wherein the patient has a serum concentration of interleukin-6 greater than 7 pg/ml.

14. The method of claim 11, wherein the administration results in a decrease of an amount of D-dimer in the patient's blood from greater than 1 μg/ml to less than 1 μg/ml.

15. A method of treatment of cytokine storm, the method comprising administering to a patient having a serum level of interleukin-6 greater than 7 pg/ml an effective amount of a pharmaceutical formulation comprising compound II.

16. The method of claim 15, wherein the patient has a serum concentration of D-dimer greater than 1 μg/ml.

17. The method of claim 15, wherein the patient has a serum concentration of interleukin-1β greater than 3 pg/ml.

18. The method of claim 15, wherein the administration results in a decrease of an amount of D-dimer in the patient's blood from greater than 1 μg/ml to less than 1 μg/ml.

19. A method of treatment of cytokine storm, the method comprising administering to a patient having a serum level of interleukin-12p70 greater than 40 pg/ml an effective amount of a pharmaceutical formulation comprising compound II.

20. The method of claim 19, wherein the patient has a serum concentration of D-dimer greater than 1 μg/ml.

21. The method of claim 19, wherein the patient has a serum concentration of interleukin-1β greater than 3 pg/ml.

22. The method of claim 19, wherein the patient has a serum concentration of interleukin-6 greater than 7 pg/ml.

23. The method of claim 19, wherein the administration results in a decrease of an amount of D-dimer in the patient's blood from greater than 1 μg/ml to less than 1 μg/ml.

24. A method of treatment of cytokine storm, the method comprising administering to a patient having a serum level of interleukin-23 greater than 15 pg/ml an effective amount of a pharmaceutical formulation comprising compound II.

25. The method of claim 24, wherein the patient has a serum concentration of D-dimer greater than 1 μg/ml.

26. The method of claim 24, wherein the patient has a serum concentration of interleukin-1β greater than 3 pg/ml.

27. The method of claim 24, wherein the patient has a serum concentration of interleukin-6 greater than 7 pg/ml.

28. The method of claim 24, wherein the administration results in a decrease of an amount of D-dimer in the patient's blood from greater than 1 μg/ml to less than 1 μg/ml.

29. A method of treatment of cytokine storm, the method comprising administering to a patient having a serum level of interleukin-27 greater than 1 ng/ml an effective amount of a pharmaceutical formulation comprising compound II.

30. The method of claim 29, wherein the patient has a serum concentration of D-dimer greater than 1 μg/ml.

31. The method of claim 29, wherein the patient has a serum concentration of interleukin-1β greater than 3 pg/ml.

32. The method of claim 29, wherein the patient has a serum concentration of interleukin-6 greater than 7 pg/ml.

33. The method of claim 29, wherein the administration results in a decrease of an amount of D-dimer in the patient's blood from greater than 1 μg/ml to less than 1 μg/ml.

34. A method of treatment of cytokine storm, the method comprising administering to a patient having a D-dimer level of greater than 1 μg/ml an effective amount of a pharmaceutical formulation comprising compound II.

35. The method of claim 34, wherein the patient has a serum concentration of interleukin-1β greater than 3 pg/ml.

36. The method of claim 34, wherein the patient has a serum concentration of interleukin-6 greater than 7 pg/ml.

37. The method of claim 34, wherein the administration results in a decrease of an amount of D-dimer in the patient's blood from greater than 1 μg/ml to less than 1 μg/ml.

* * * * *